US008128886B2

United States Patent
Appel et al.

(10) Patent No.: US 8,128,886 B2
(45) Date of Patent: Mar. 6, 2012

(54) REACTOR FOR PREPARING ORGANIC PEROXIDES VIA THE INTERMEDIATE OF A SOLID HYDROPEROXIDE

(75) Inventors: Hans Appel, Penzberg (DE); Joseph Weinmaier, Mühldorf (DE)

(73) Assignee: United Initiators GmbH & Co. KG, Pullach (DE)

( * ) Notice: Subject to any disclaimer, the term of this patent is extended or adjusted under 35 U.S.C. 154(b) by 408 days.

(21) Appl. No.: 11/989,760

(22) PCT Filed: Jul. 18, 2006

(86) PCT No.: PCT/EP2006/064359
§ 371 (c)(1),
(2), (4) Date: May 30, 2008

(87) PCT Pub. No.: WO2007/014845
PCT Pub. Date: Feb. 8, 2007

(65) Prior Publication Data
US 2009/0187048 A1    Jul. 23, 2009

(30) Foreign Application Priority Data

Aug. 1, 2005  (DE) .......................... 10 2005 036 055

(51) Int. Cl.
*C07C 407/00* (2006.01)
*C07C 409/04* (2006.01)
*C07C 409/16* (2006.01)

(52) U.S. Cl. ........ 422/239; 422/211; 422/212; 210/225; 210/226; 210/767; 210/768; 210/770; 568/558; 568/562; 568/565; 568/568

(58) Field of Classification Search .................. 422/239, 422/211, 212; 210/225, 226, 633, 767, 768; 210/770; 568/558, 562, 565, 568
See application file for complete search history.

(56) References Cited

U.S. PATENT DOCUMENTS

| 3,117,166 | A |   | 1/1964  | Harrison et al. |
|-----------|---|---|---------|-----------------|
| 3,911,020 | A | * | 10/1975 | Cooper .......................... 568/565 |
| 4,056,363 | A | * | 11/1977 | Messner ....................... 422/252 |
| 5,210,320 | A |   | 5/1993  | Tso et al. |

(Continued)

FOREIGN PATENT DOCUMENTS

CN    1070844 A    4/1993

(Continued)

OTHER PUBLICATIONS

International Search Report for PCT/EP2006/064359.

(Continued)

*Primary Examiner* — Walter D Griffin
*Assistant Examiner* — Huy-Tram Nguyen
(74) *Attorney, Agent, or Firm* — Law Office of: Michael A. Sanzo, LLC

(57) ABSTRACT

A reactor which comprises a vessel (1) with a vessel bottom (2), a stirrer (3) arranged in the vessel, an emergency discharge valve (4) arranged in the vessel bottom for emptying the reactor in less than 600 seconds and at least one filtration device (5) arranged in the vessel bottom is suitable for the safe preparation of organic peroxides. The process for preparing an organic peroxide comprises the steps of preparing a solid hydroperoxide in the form of a suspension in the reactor, filtering the suspension through the filtration device (5) arranged in the vessel bottom (2) while retaining the solid hydroperoxide in the reactor and reacting the hydroperoxide with an alkylating agent, an acylating agent or a carbonyl compound.

23 Claims, 2 Drawing Sheets

U.S. PATENT DOCUMENTS

| | | | |
|---|---|---|---|
| 5,290,359 A * | 3/1994 | Coonen et al. | 118/712 |
| 5,856,586 A | 1/1999 | Hagel et al. | |
| 6,177,008 B1 * | 1/2001 | Treiber et al. | 210/198.2 |
| 7,666,315 B2 * | 2/2010 | Lopez Martinez et al. | 210/759 |
| 2002/0016494 A1 * | 2/2002 | Yoneda et al. | 560/207 |
| 2005/0031530 A1 | 2/2005 | Martin | |
| 2006/0153757 A1 * | 7/2006 | Cooper et al. | 422/243 |
| 2007/0081922 A1 * | 4/2007 | Blum et al. | 422/129 |

FOREIGN PATENT DOCUMENTS

| | | |
|---|---|---|
| CN | 1240787 A | 1/2000 |
| EP | 0 014 802 A1 | 9/1980 |
| FR | 2 806 928 A1 | 10/2001 |
| JP | 2000204391 A * | 7/2000 |

OTHER PUBLICATIONS

Written Opinion of the International Searching Authority for PCT/EP2006/064359.

Ulmann, et al., Ullmann's Encyclopedia of Industrial Chemistry, vol. B2, pp. 10-47-10-48 (1988).

English language abstract for CN 1070844A.

English language abstract for CN 1240787A.

English language translation of the Written Opinion of the International Searching Authority for PCT/EP2006/064359 filed Jul. 18, 2006.

English language translation of the International Preliminary Report on Patentability for PCT/EP2006/064359 filed Jul. 18, 2006.

English language abstract for FR 2 806 928 A1.

* cited by examiner

REACTOR FOR PREPARING ORGANIC PEROXIDES VIA THE INTERMEDIATE OF A SOLID HYDROPEROXIDE

CROSS REFERENCE TO RELATED APPLICATIONS

The present application is U.S. national stage of international application PCT/EP2006/064359, which had an international filing date of Jul. 18, 2006, and which was published in German under PCT Article 21(2) on Feb. 8, 2007. The international application claims priority to German application 10 2005 036 055.6, filed on Aug. 1, 2005. These prior applications are hereby incorporated by reference in their entirety.

The invention is directed to a reactor for preparing organic peroxides via the intermediate of a solid hydroperoxide, and to processes for preparing organic peroxides using this reactor.

Organic peroxides find industrial use as initiators for polymerization reactions, for crosslinking reactions of polymers and for the curing of unsaturated polyester resins. These applications are based on the decomposition of the peroxides at the labile oxygen-oxygen bond into free radicals. Depending on the chemical structure of the peroxide, this decomposition proceeds at different temperatures and with a different rate. In the case of inadequate heat removal, the heat released in the course of decomposition leads to self-acceleration of the decomposition process, which merges into a usually violent decomposition. Thus, many peroxides in pure form or in high concentration are explosive substances. The handling of solid peroxides, for which the decomposition can be initiated not just thermally but also by mechanical stress, for example by friction or by shock, is particularly problematic.

For numerous organic peroxides of industrial interest, the preparation is effected via the intermediate of a solid hydroperoxide which for further reaction has to be removed from the liquid reaction mixture in which it was prepared. One example is that of the derivatives of the solid 2,5-dimethylhexane-2,5-dihydroperoxide known from U.S. Pat. No. 3,117,166. In order to be able to prepare these products safely on the industrial scale, apparatus and processes are required with which the reaction can be carried out under conditions under which the solid hydroperoxide is subjected only to little mechanical stress.

U.S. Pat. No. 5,210,320 describes a one-stage process for preparing derivatives of 2,5-dimethylhexane-2,5-dihydroperoxide in which the unconverted feedstocks are removed from the solid hydroperoxide, and the hydroperoxide is optionally washed and then reacted further. Methods mentioned in the description for removing the solid hydroperoxide are decanting, filtration and centrifugation, preference being given to decanting. Example 2 discloses the preparation of 2,5-dimethyl-2,5-di(tert-butylperoxy)hexane in a stirred 500 ml jacketed reactor, wherein the solid 2,5-dimethylhexane-2,5-dihydroperoxide intermediate is removed from the feedstocks and the wash liquid by decanting and the solid remains in the reactor. However, such a removal by decanting has the disadvantage that a large amount of liquid remains in the solid, so that the removal is not particularly effective and several washing steps become necessary. The document gives no indication of how a removal of the solid hydroperoxide with retention of the hydroperoxide in the reactor can be performed industrially in a safe manner.

The prior art, for example Ullmanns Encyclopedia of Industrial Chemistry, Fifth Edition, Volume B2, page 10-47, discloses cooled stirred suction filters in which the bottom of the reactor vessel is designed as a filtration unit and in which a reaction and a filtration can be carried out in succession while retaining the solid. However, this apparatus is not suitable for the safe preparation of organic peroxides for safety reasons, since it cannot be emptied rapidly enough in the event of failure of the cooling during the reaction and the risk therefore exists of a self-accelerating reaction in the reactor with catastrophic consequences.

It is therefore an object of the invention to provide a reactor which solves this safety problem and in which the preparation of organic peroxides via the intermediate of a solid hydroperoxide enables a better removal of the solid hydroperoxide from the feedstocks.

The invention provides a reactor for preparing organic peroxides, comprising
a) a vessel with a vessel bottom
b) a stirrer arranged in the vessel
c) an emergency discharge valve arranged in the vessel bottom for emptying the reactor in less than 600 seconds and
d) at least one filtration device arranged in the vessel bottom.

The invention also provides a process for preparing an organic peroxide, comprising the steps of
a) preparing a solid hydroperoxide in the form of a suspension in the inventive reactor,
b) filtering the suspension through the filtration device arranged in the vessel bottom while retaining the solid hydroperoxide in the reactor and
c) reacting the hydroperoxide with an alkylating agent, an acylating agent or a carbonyl compound.

The inventive reactor comprises a vessel with a vessel bottom, the vessel preferably having the form of an upright cylinder and the vessel bottom preferably being designed curved in the form of a so-called dished bottom. In a preferred embodiment, the vessel additionally has a cooling jacket through which a cooling medium can be passed in order to cool the vessel contents.

The inventive reactor further comprises a stirrer arranged in the vessel, with which a reaction mixture disposed in the reactor can be mixed. The stirrer is preferably driven by means of a shaft from the top side of the reactor. Suitable stirrers are all stirrers usable for the mixing of liquids. Preference is given to using a paddle stirrer whose paddles reach to just above the vessel bottom, the distance of the stirrer from the vessel bottom in particular being such that the filter cake formed in the filtration just fails to reach the paddles of the stirrer. On the one hand, such an arrangement of the stirrer allows the mechanical stress on the solid in the filtration to be kept low, and on the other hand, the solid can be stirred up even with small amounts of wash liquid and hence be washed effectively.

The inventive reactor also comprises an emergency discharge valve arranged in the vessel bottom for emptying the reactor in less than 600 seconds. The time for the emptying of the reactor is determined in accordance with the invention for an emptying of the reactor filled with water to an extent of 90% with fully opened emergency discharge valve with no difference between internal reactor pressure and exterior pressure. The emergency discharge valve is preferably arranged at the lowest point of the vessel bottom in order to be able to completely empty the vessel. In the preferred embodiment of the vessel bottom as a curved dished bottom, the emergency discharge valve is preferably arranged in the middle of the vessel bottom. The inventive emergency discharge valve is preferably designed in such a way that opening of the valve can be achieved over the entire valve cross section within a short time, for example by designing the emergency discharge valve as a ball valve, as a flap or as a vane. The emergency discharge valve can be used to empty the reactor safely in the event of operational disruption or of a decomposition of an organic peroxide starting in the reactor, before a self-accelerating and uncontrolled decomposition of the organic peroxide occurs. The emergency discharge valve is preferably designed in such a way that the reactor can be emptied within less than 180 seconds, in particular within less than 60 seconds. As a result of shorter emptying times, the reactor can still be operated safely even at higher reaction temperatures and higher heat release rates.

Opening of the emergency discharge valve is preferably triggered by means of a temperature and/or pressure measurement in the reactor. The additional possibility of triggering by the operator of the plant is also appropriate. What is also appropriate is the connection of the emergency discharge valve with a collecting vessel in which the discharged reactor contents are diluted with an inert diluent, for example water, and cooled if appropriate.

The inventive reactor finally also comprises at least one filtration device arranged in the vessel bottom, by means of which liquid can be removed from the reactor, while retaining solid present in the liquid in the reactor interior. The filtration device arranged in the vessel bottom is preferably designed in the form of one or more frits composed of a porous, dimensionally stable material. Suitable material for such frits is glass, ceramic and metal, in particular stainless steel. Filtration devices in the form of frits are preferably designed such that each frit is arranged flush in the vessel bottom, i.e. the side of the frit facing towards the reactor interior is flush with the inside of the vessel bottom of the reactor.

The filtration devices arranged in the vessel bottom appropriately also comprise in each case at least one line for withdrawing liquid which has passed through the filter element, as well as a shutoff device between the frit and the withdrawal line which can be used to prevent liquid from passing unintentionally from the reactor into the withdrawal line. The filtration device is preferably designed in such a way that the volume between the filter element and the shutoff device is kept as small as possible.

In a preferred embodiment, the filtration device is arranged so as to be exchangeable in an orifice in the vessel bottom. The orifice is appropriately designed as a round flange orifice with which the filtration device is connected by means of screws.

In a further preferred embodiment, the reactor additionally comprises at least one cooling device which is arranged in the vessel bottom and projects into the interior of the vessel. The cooling device is preferably arranged in such a way that the predominant portion of the cooling surface is close to the vessel bottom, so that effective cooling is achieved in the event of only partial filling of the reactor. The cooling device is preferably designed as a heat exchanger flowed through by a cooling medium, especially as pipe coil, tube bundle heat exchanger or plate heat exchanger. The cooling device can be arranged below the stirrer or preferably beside the stirrer.

In the embodiment of the reactor with filtration devices arranged so as to be exchangeable, preference is given to using cooling devices which are exchangeable with the filtration devices. Particular preference is given to using tube bundle heat exchangers which have a floating head and are installed in the vessel from below through an orifice in the vessel bottom. In this embodiment of the reactor, the cooling output of the reactor can be adjusted in each case to the cooling requirement of the reaction carried out in the reactor by exchanging some of the filtration devices for cooling devices.

The inventive reactor enables safe preparation and further reaction of solid hydroperoxides, in which the hydroperoxides are exposed only to low mechanical stresses and in which a decomposition of the hydroperoxide beginning in the reactor can at any time be controlled rapidly and safely by emptying the reactor.

The process according to the invention for preparing an organic peroxide is effected via the intermediate of a solid hydroperoxide. In the first step of the process, the solid hydroperoxide is prepared in the reactor according to the invention in the form of a suspension. This suspension is prepared by known processes. The solid hydroperoxide prepared is preferably 2,5-dimethylhexane-2,5-dihydroperoxide.

A preferred method of preparing a suspension of a solid hydroperoxide is the reaction of a tertiary alcohol with hydrogen peroxide in an acidic medium. To prepare 2,5-dimethylhexane-2,5-dihydroperoxide, 2,5-dimethylhexane-2,5-diol is reacted in this method with hydrogen peroxide, preferably with addition of sulphuric acid. Suitable reaction conditions for this reaction are known from U.S. Pat. No. 3,117,166 and U.S. Pat. No. 5,210,320.

A further preferred method for preparing 2,5-dimethylhexane-2,5-dihydroperoxide is the reaction of 2,5-dimethyl-1,5-hexadiene with hydrogen peroxide in an acidic medium, known from WO 96/03372. In this embodiment, the inventive reactor is preferably used in the embodiment with additional cooling device in order to be able to remove the high heat of reaction in the preparation of the hydroperoxide safely and rapidly.

During the preparation of the suspension of the solid hydroperoxide, the passage of liquid through the filtration device arranged in the reactor bottom is preferably prevented either by virtue of a shutoff device arranged beyond the filtration device remaining closed or by passing a gas stream into the reactor which counteracts the passage of liquid through the filtration device.

In the second step of the process according to the invention, the suspension of the solid hydroperoxide is then filtered through the filtration device arranged in the vessel bottom, the solid hydroperoxide being retained in the reactor and the liquid being withdrawn from the reactor. The filtration is preferably brought about by applying a reduced pressure to the filtration device, so that the liquid is forced through the filtration device by the pressure in the reactor.

The solid hydroperoxide retained in the reactor can additionally also be washed with a wash liquid in order to remove adhering feedstocks before it is reacted further. The wash liquid is selected such that it dissolves the hydroperoxide only to a slight extent but the feedstocks to be removed readily. Suitable wash liquids for 2,5-dimethylhexane-2,5-dihydroperoxide are water, aqueous sodium sulphate solution or aqueous ammonium sulphate solution. To this end, the solid hydroperoxide is preferably suspended in the wash liquid, appropriately using the stirrer arranged in the reactor in order to obtain a uniform suspension. The resulting suspension is then filtered through the filtration device arranged in the vessel bottom while retaining the solid hydroperoxide in the reactor.

In the process according to the invention, the hydroperoxide retained in the reactor is subsequently reacted with an alkylating agent, an acylating agent or a carbonyl compound to give the desired organic peroxide. The reaction conditions required for this reaction are known from the prior art. In this step, the hydroperoxide is preferably dissolved in a solvent before it is reacted with the alkylating agent, the acylating agent or the carbonyl compound, in order to be able to remove the heat of reaction released in the reaction safely. The reaction with the alkylating agent, the acylating agent or the carbonyl compound can be effected in the inventive reactor.

Alternatively, the hydroperoxide can also be dissolved or suspended in a solvent and transferred into another reactor in order to carry out the reaction there with the alkylating agent, the acylating agent or the carbonyl compound.

In a preferred embodiment of the process according to the invention, the alkylating agent used is a tertiary alcohol and the reaction of the hydroperoxide with the tertiary alcohol is effected in the presence of a strong acid. The tertiary alcohols used are preferably tert-butanol, tert-amyl alcohol or cumyl alcohol. Suitable reaction conditions for this reaction are known from U.S. Pat. No. 5,210,320. In a particularly preferred embodiment of the process, the product 2,5-dimethyl-2,5-di(tert-butylperoxy)hexane is obtained via the intermediate 2,5-dimethylhexane-2,5-dihydroperoxide by reacting with tert-butanol in the presence of sulphuric acid.

In further preferred embodiments of the process according to the invention, the hydroperoxide is reacted with an acylating agent from the group of the carbonyl chlorides, carboxylic anhydrides and chloroformates. Suitable reaction conditions for the reactions are known from U.S. Pat. No. 3,117,166.

The acylating agent used is preferably a carboxylic acid chloride from the group of acetyl chloride, isobutyryl chloride, pivaloyl chloride, 2-ethylhexanoyl chloride, 3,5,5-trimethylhexanoyl chloride, neodecanoyl chloride and benzoyl chloride. In a particularly preferred embodiment of the process, one of the compounds 2,5-dimethyl-2,5-di(acetylperoxy)hexane, 2,5-dimethyl-2,5-di(isobutyrylperoxy)hexane, 2,5-dimethyl-2,5-di(pivaloylperoxy)hexane, 2,5-dimethyl-2,5-di(2-ethylhexanoylperoxy)hexane, 2,5-dimethyl-2,5-di(3,5,5-trimethylhexanoylperoxy)hexane or 2,5-dimethyl-2,5-di(benzoylperoxy)hexane is prepared via the 2,5-dimethylhexane-2,5-dihydroperoxide intermediate by reacting with one of these preferred carboxylic acid chlorides.

In a further preferred embodiment, the acylating agent used is preferably a chloroformate from the group of isopropyl chloroformate, n-butyl chloroformate, sec-butyl chloroformate, 2-ethylhexyl chloroformate, myristyl chloroformate, cetyl chloroformate, cyclohexyl chloroformate and 4-tert-butylcyclohexyl chloroformate. In a particularly preferred embodiment of the process, one of the compounds 2,5-dimethyl-2,5-di(isopropyloxy-carbonylperoxy)hexane, 2,5-dimethyl-2,5-di(n-butyloxy-carbonylperoxy)hexane, 2,5-dimethyl-2,5-di(sec-butyl-oxycarbonylperoxy)hexane, 2,5-dimethyl-2,5-di(2-ethyl-hexyloxycarbonylperoxy)hexane, 2,5-dimethyl-2,5-di(myristyloxycarbonylperoxy)hexane, 2,5-dimethyl-2,5-di(cetyloxycarbonylperoxy)hexane, 2,5-dimethyl-2,5-di(cyclohexyloxycarbonylperoxy)hexane or 2,5-dimethyl-2,5-di(4-tert-butylcyclohexyloxy-carbonylperoxy)hexane is prepared via the 2,5-dimethylhexane-2,5-dihydroperoxide intermediate by reacting with one of these preferred chloroformates.

In a further preferred embodiment, the carbonyl compound used is acetone. In a particularly preferred embodiment of the process, the compound 3,3,6,6,9,9-hexamethylcyclo-1,2,4,5-tetraoxanonane is prepared via the 2,5-dimethylhexane-2,5-dihydroperoxide intermediate by reacting with acetone.

The process according to the invention for preparing organic peroxides via the intermediate of a solid hydroperoxide affords products with improved purity, since it enables more effective removal of the solid hydroperoxide from the substances used for its preparation. As a result of the more effective washing of the solid hydroperoxide, it is also possible to reduce the amount of wash liquid required for washing, so that less waste occurs in the process according to the invention.

Figure 1:
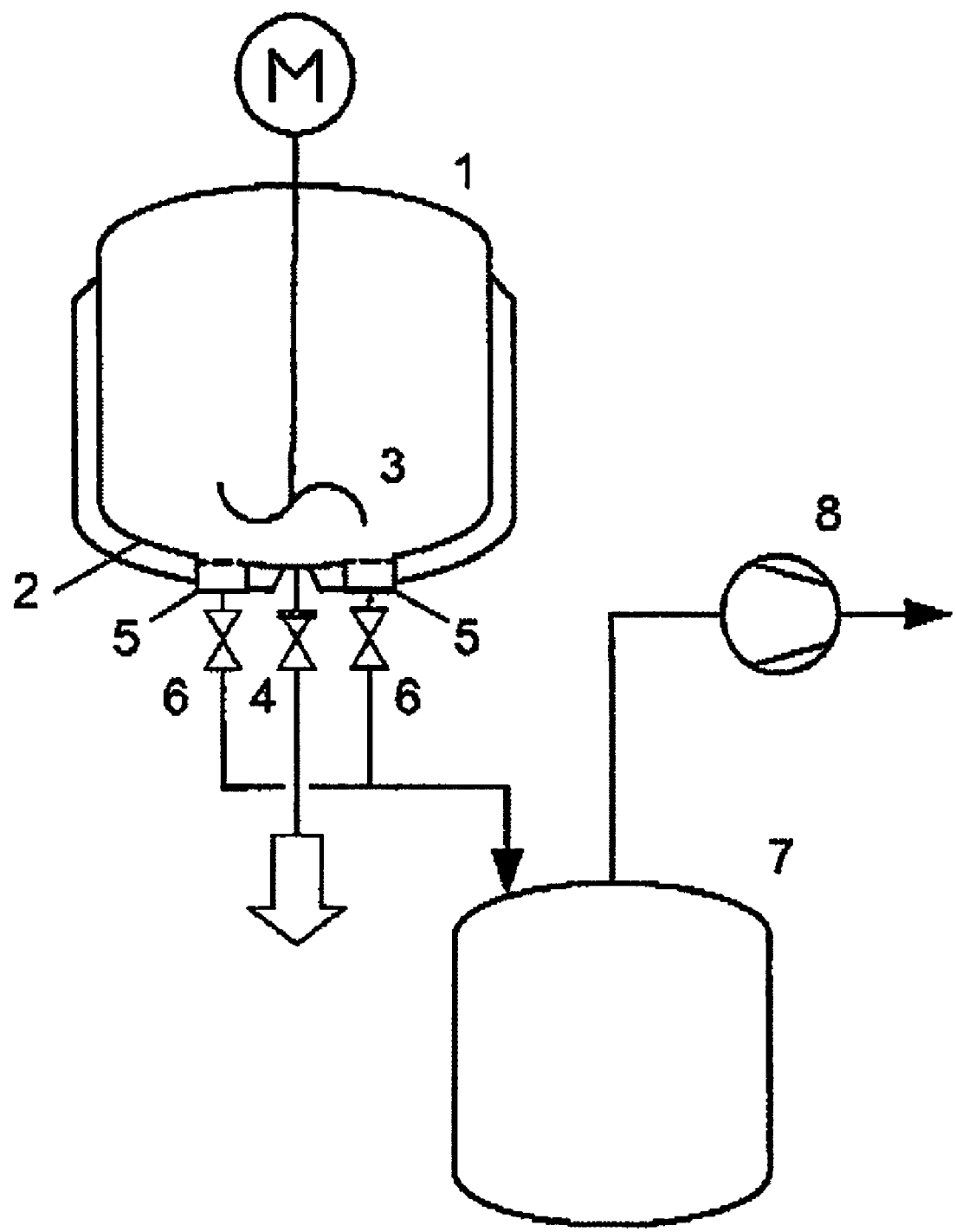
FIG. 1 shows one embodiment of the inventive reactor.

In the embodiment shown in FIG. 1, the inventive reactor has a vessel (1) in the form of a cylindrical jacketed vessel whose vessel bottom (2) is designed as a dished bottom. The vessel (1) has a filling height of 120 cm and an internal diameter of 120 cm. A stirrer (3) driven from above in the form of an impeller stirrer, whose blades reach up to 18 cm above the vessel bottom, is arranged in the vessel. An emergency discharge valve (4) with a diameter of the discharge orifice of 18 cm is arranged centrally in the vessel bottom (2). The vessel bottom additionally has four flange orifices each with a diameter of 21 cm. A filtration device (5) which has a metal sinter plate over the entire orifice cross section is installed into each of the flange orifices, the metal sinter plate in the installed state being flush with the inner wall of the vessel (1). Each filtration device is connected via a shutoff valve (6) and connecting lines with a collecting vessel (7) for liquid and a vacuum pump (8).

The volume between metal sinter plate and shutoff valve is approx. 1 l per filtration device.

Figure 2:
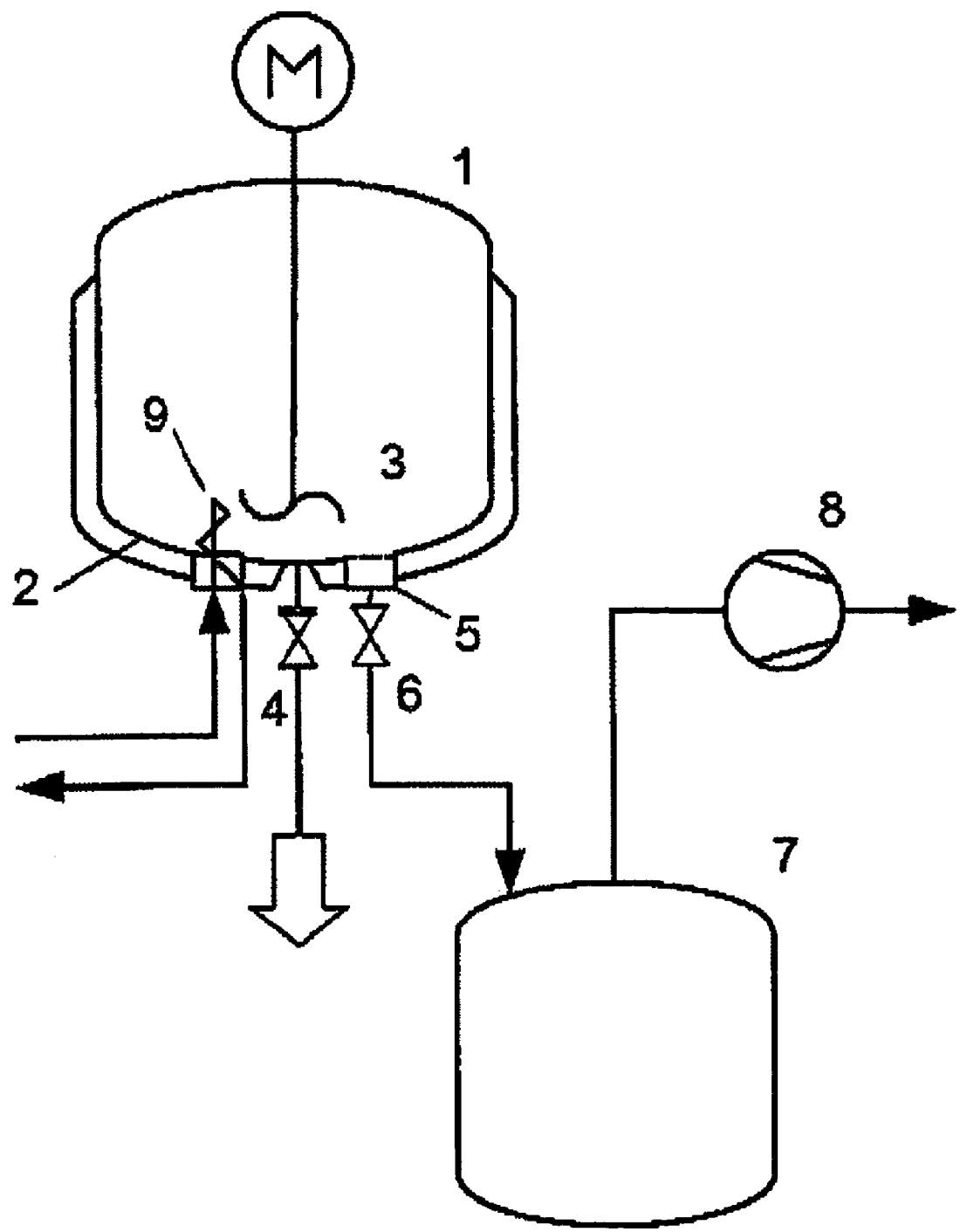
FIG. 2 show an alternative embodiment of the inventive reactor with an additional cooling device.

In the embodiment shown in FIG. 2, the inventive reactor has an additional cooling device (9) arranged in the vessel bottom (2), which projects into the interior of the vessel. The cooling device (9) may have the form of a pipe coil, of a tube bundle or of a plate heat exchanger. The cooling device (9) is designed so as to be exchangeable with the filtration device (5).

EXAMPLE

Preparation of
2,5-dimethyl-2,5-di(tert-butylperoxy)hexane

A reactor corresponding to FIG. 1 was initially charged with a mixture of 550 kg of 70% by weight hydrogen peroxide and 366 kg of 80% by weight sulphuric acid. With stirring and cooling of the reactor through the jacket, 250 kg of 2,5-dimethyl-2,5-hexanediol were metered in within 60 min, in the course of which the temperature rose from 20° C. to 30-32° C. The reaction mixture was stirred at 30° C. for another 90 min and then admixed with 200 kg of water. The stirrer was then switched off and the suspension formed was filtered within 10 min by applying reduced pressure to the filtration devices (5), in the course of which the liquid phase was sucked into the collecting vessel (7) and the precipitated 2,5-dimethylhexane-2,5-dihydroperoxide was retained in the vessel (2). The solid product retained in the reactor was washed by adding 500 kg of water, stirring the suspension for 3 min and filtering again by applying reduced pressure to the filtration devices (5). This washing operation was repeated once more. Thereafter, 481 kg of tert-butanol were added and the solid was dissolved therein by stirring and heating. 500 kg of 80% by weight sulphuric acid were metered into the resulting solution within 60 min with stirring and cooling of the reactor through the jacket, in the course of which the temperature rose to from 40 to 45° C. The reaction mixture was stirred at this temperature for a further 60 min and then admixed with 50 kg of water. The lower aqueous phase was removed and the liquid product was washed successively with 150 kg of water, 150 kg of 1% by weight sodium hydroxide solution and 150 kg of water, by stirring the phases and then removing the lower aqueous phase. After removal of residual water and volatile by-products by stripping under reduced pressure in a stripping column, 405 kg (90%) of 2,5-dimethyl-2,5-di(tert-butylperoxy)hexane were obtained.

The invention claimed is:

1. A reactor for preparing organic peroxides, comprising:
   a) a vessel (1) with a vessel bottom (2) and comprising a stirrer (3);
   b) at least one filtration device (5) located in said vessel bottom;
   c) an emergency discharge valve (4) located in said vessel bottom and a separate shutoff valve (6); wherein:
      i) said shutoff valve (6) is positioned so that fluid passing from said vessel (1) through said shutoff valve (6) also passes through said filtration device (5);
      ii) said emergency discharge valve (4) is positioned so that fluid passing from said vessel (1) through said emergency discharge valve (4) does not pass through said filtration device (5).

2. The reactor of claim 1, wherein said filtration device (5) is a frit which is flush in said vessel bottom (2).

3. The reactor of claim 1, wherein said emergency discharge valve is a valve for emptying the reactor in less than 600 seconds.

4. The reactor of claim 1, further comprising at least one cooling device (9) located in said vessel bottom (2) and projecting into the interior of said vessel (1).

5. A process for preparing an organic peroxide, comprising the steps of:
   a) preparing a solid hydroperoxide in the form of a suspension in the reactor of claim 1;
   b) filtering the suspension through the filtration device (5) located in the vessel bottom (2) while retaining the solid hydroperoxide in the reactor; and
   c) reacting the hydroperoxide with an alkylating agent, an acylating agent or a carbonyl compound.

6. The process of claim 5, wherein said solid hydroperoxide is 2,5-dimethylhexane-2,5-dihydroperoxide.

7. The process of claim 5, wherein said solid hydroperoxide is suspended in a wash liquid between step b) and step c) and the resulting suspension is filtered through said filtration device (5) located in the vessel bottom (2) while retaining the solid hydroperoxide in the reactor.

8. The process of claim 5, wherein, in step c), said hydroperoxide is reacted with a tertiary alcohol in the presence of a strong acid.

9. The process of claim 5, wherein, in step c), said hydroperoxide is reacted with an acylating agent selected from the group consisting of: a carboxylic acid chloride; a carboxylic anhydride; and a chloroformate.

10. The process of claim 9, wherein said acylating agent is a carboxylic acid chloride selected from the group consisting of: acetyl chloride; isobutyryl chloride; pivaloyl chloride; 2-ethylhexanoylchloride; 3,5,5-trimethylhexanoyl chloride; neodecanoyl chloride; and benzoyl chloride.

11. The process of claim 9, wherein said acylating agent is a chloroformate selected from the group consisting of: isopropyl chloroformate; n-butyl chloroformate; sec-butyl chloroformate; 2-ethylhexyl chloroformate; myristyl chloroformate; cetyl chloroformate; cyclohexyl chloroformate; and 4-tert-butylcyclohexyl chloroformate.

12. The process of claim 5, wherein, in step c), said hydroperoxide is reacted with acetone.

13. A reactor for preparing organic peroxides, comprising:
   a) a vessel (1) with a vessel bottom (2) and comprising a stirrer (3);
   b) an emergency discharge valve (4) located in said vessel bottom (2);
   c) at least one filtration device (5) located in said vessel bottom (2); and
   d) at least one cooling device (9) located in said vessel bottom (2) and projecting into the interior of said vessel (1).

14. The reactor of claim 13, wherein said filtration device (5) is a frit which is flush in said vessel bottom (2).

15. The reactor of claim 13, wherein said emergency discharge valve is a valve for emptying the reactor in less than 600 seconds.

16. A process for preparing an organic peroxide, comprising the steps of:
   a) preparing a solid hydroperoxide in the form of a suspension in the reactor of claim 13;
   b) filtering the suspension through the filtration device (5) located in the vessel bottom (2) while retaining the solid hydroperoxide in the reactor; and
   c) reacting the hydroperoxide with an alkylating agent, an acylating agent or a carbonyl compound.

17. The process of claim 16, wherein said solid hydroperoxide is 2,5-dimethylhexane-2,5-dihydroperoxide.

18. The process of claim 16, wherein said solid hydroperoxide is suspended in a wash liquid between step b) and step c) and the resulting suspension is filtered through said filtration device (5) located in the vessel bottom (2) while retaining the solid hydroperoxide in the reactor.

19. The process of claim 16, wherein, in step c), said hydroperoxide is reacted with a tertiary alcohol in the presence of a strong acid.

20. The process of claim 16, wherein, in step c), said hydroperoxide is reacted with an acylating agent selected from the group consisting of: a carboxylic acid chloride, a carboxylic anhydride; and a chloroformate.

21. The process of claim 20, wherein said acylating agent is a carboxylic acid chloride selected from the group consisting of: acetyl chloride; isobutyryl chloride; pivaloyl chloride; 2-ethylhexanoylchloride; 3,5,5-trimethylhexanoyl chloride; neodecanoyl chloride; and benzoyl chloride.

22. The process of claim 20, wherein said acylating agent is a chloroformate selected from the group consisting of: isopropyl chloroformate; n-butyl chloroformate; sec-butyl chloroformate; 2-ethylhexyl chloroformate; myristyl chloroformate; cetyl chloroformate; cyclohexyl chloroformate; and 4-tert-butylcyclohexyl chloroformate.

23. The process of claim 20, wherein, in step c), said hydroperoxide is reacted with acetone.

* * * * *